United States Patent [19]

Amin

[11] Patent Number: 5,792,159
[45] Date of Patent: Aug. 11, 1998

[54] TONGUE CLEANER

[76] Inventor: Jatin N. Amin, 6 Dayton Dr., Apt. No. 20-A, Edison, N.J. 08820

[21] Appl. No.: 780,901
[22] Filed: Jan. 9, 1997

Related U.S. Application Data

[60] Provisional application No. 60/016,023 Apr. 23, 1996.
[51] Int. Cl.⁶ .................................................. A61B 17/24
[52] U.S. Cl. ........................................ 606/161; 15/236.06
[58] Field of Search ................................... 606/162, 161; 15/236.06, 236.05

[56] References Cited

U.S. PATENT DOCUMENTS

| | | | |
|---|---|---|---|
| D. 265,506 | 7/1982 | Finamore | D24/23 |
| D. 285,342 | 8/1986 | Audette | D24/23 |
| D. 332,352 | 1/1993 | Caldwell et al. | D4/104 |
| D. 360,262 | 7/1995 | Ly | D24/147 |
| D. 367,707 | 3/1996 | Baker | D24/147 |
| 2,583,750 | 1/1952 | Runnels . | |
| 4,455,704 | 6/1984 | Williams | 15/111 |
| 5,061,272 | 10/1991 | Reese | 606/161 |
| 5,226,197 | 7/1993 | Nack et al. | 15/111 |
| 5,445,825 | 8/1995 | Copelan et al. | 424/448 |

FOREIGN PATENT DOCUMENTS

| | | |
|---|---|---|
| 659404 | 6/1929 | France . |
| 580878 | 6/1933 | Germany . |

*Primary Examiner*—Michael H. Thaler
*Attorney, Agent, or Firm*—Richard C. Litman

[57] ABSTRACT

A tongue cleaning device for personal use or use by an oral hygiene professional. The device has a relatively flat cleaning head integral with a handle that preferably is angled to permit ease of use without causing tissue damage. The cleaning head is provided with a plurality of cleaning ribs that extend the length of the cleaning head, which is oriented perpendicular to the handle. Each of the cleaning ribs depends from a lower surface of the cleaning head, and each has a cleaning surface configured for removing unhealthy films and deposits from the tongue. To reduce the likelihood of damaging tissues of the mouth, the ribs are configured without harsh or rough edges, and the cleaning head is flattened so that the user will not scrape the rear portion of the soft palate. The tongue cleaning device of the present invention is made from a polymeric material, such as a food grade plastic, that will withstand temperatures necessary for sterilization.

13 Claims, 4 Drawing Sheets

TONGUE CLEANER

BACKGROUND OF THE INVENTION

This application is based upon Provisional Pat. application Ser. No. 60/016,023, filed Apr. 23, 1996.

1. Field of the Invention

The present invention is a tongue cleaner constructed from polymeric material, which can be sterilized, the cleaner having a plurality of cleaning ridges. Further, the present invention is constructed from molded or extruded materials suitable for hygienic human use. The tongue cleaner is configured for easy personal use or use by an oral hygiene professional.

2. Description of the Prior Art

It is well established that a regular practice of oral hygiene should include the removal of unhealthy and often malodorous oral deposits and exudates from the surface of the tongue. The prior art contains numerous examples of apparatus and designs for cleaning the tongue, however, currently available devices are likely to damage lingual cilium, tear the tongue, and create microlesions. Such damage can lead to an increased risk of bacterial, fungal, yeast or viral infections. When properly used, the specifically configured cleaning ribs of the present invention provide gentle, non-abrasive cleaning surfaces.

Several prior art tongue cleaners or scrapers utilize a single sharp scraping edge to effect the desired cleaning of the tongue. Tongue scrapers having a single sharp edge are objectionable because they are likely to abrade the surface of the tongue or, in the event of an accident, to cut or tear the soft tissue lining of the cheeks. Not only is a single sharp edge likely to damage the surface tissue of the tongue and cheeks, but it also may produce great physical discomfort for the user. Exemplary prior art containing such sharp scraping edges are disclosed in U.S. Pat. No. D265,506 which issued to Peter G. Finamore on Jul. 20, 1982; U.S. Pat. No. D285,342 which issued to Clifford J. Audette on Aug. 26, 1986; U.S. Pat. No. D360,262 which issued to Toan K. Ly on Jul. 11, 1995; and U.S. Pat. No. D367,707 which issued to Stephen M. Baker on Mar. 5, 1996. U.S. Pat. No. 2,583,750, which issued to Garland D. Runnels on Jan. 29, 1952, discloses a tongue cleaning device that has a number of sharp edges for cleaning debris from the surface of the tongue. Although the device is fabricated from a polymerized hydrocarbon, no hygienic materials are described.

In addition, many of the currently available tongue cleaning devices are uncomfortable and unpleasant to use. Discomfort, such as gagging or retching, discourages regular tongue cleaning. The present invention overcomes this disadvantage with an angled head having cleaning ribs that are pleasant to use. Thus, the present invention encourages regular oral hygiene. The invention encourages tongue cleaning to become an accepted daily constitutional and morning ritual, just as taking a shower and brushing one's teeth are all part of an essential routine for commencing a new day.

Another type of cleaning surface is the brush having a number of bristles for cleaning the tongue. However, the effect of brushing also may create physical discomfort for many persons, and even gagging and retching, particularly with children. Prior art tongue cleaners that utilize bristled brushes include U.S. Pat. No. D332,352 which issued to Carlene Caldwell et al. on Jan. 12, 1993, and U.S. Pat. No. 5,226,197 which issued to Rachel Nack et al. on Jul. 13, 1993.

The prior art also contains numerous other examples of tongue scrapers and cleaners. U.S. Pat. No. 4,455,704, which issued to Robert L. Williams on Jun. 26, 1984, describes a toothbrush with a tongue scraper. This device is unsuitable for professional use because it cannot be sterilized - an imperative quality when the present invention is used professionally. U.S. Pat. No. 5,061,272, which issued to Sandra C. Reese on Oct. 29, 1991, discloses a stainless steel scraping device that has an extremely narrow scraping edge. Such a narrow scraping device necessitates repetitive scraping motion across the surface of the tongue, which young children in particular would find exceedingly unpleasant. U.S. Pat. No. 5,445,825, which issued to Phoebe Copelan et al. on Aug. 29, 1995, discloses a disposable personal dental hygiene assembly. According to one embodiment, the assembly comprises a wedge shaped head having a plurality of transverse ribs for cleaning and massaging the gums and tongue. However, because the wedge shaped head tapers to a point and the head is not angled with respect to the handle, it is difficult to reach the back of the tongue with such an assembly.

French Brevet D'Invention No. 659,404 published by Funke Aktiengesellschaft on Jun. 28, 1929, describes a number of embodiments of a device for cleaning the tongue. The device can be made of several materials including whale bone and wood; however, none of the embodiments include a device constructed from hygienic material that can be sterilized. Moreover, all of the embodiments have a single scraping edge which subjects each of the embodiments to the above-mentioned problems. German Patentschrift No. 580,878, which issued on Jun. 29, 1933, to Anton Rothstein, describes a tongue scraper that is "U" shaped and, consequently, particularly difficult to use.

None of the prior art enables or teaches one skilled in the art to make a tongue cleaner having the broadened nonacute cleaning surfaces or the hygienic qualities of the present invention. The present invention combines unique characteristics of construction and configuration. It is constructed from sanitary materials and configured in an efficacious manner to permit the user to cleanse the tongue in manner that is both safe and comfortable. When the present invention is applied to the tongue, the multiple broad cleaning ribs dissipate the pressure across the surface of the tongue, rather than focusing pressure upon an acute location. The gag reflex is thus greatly reduced, or altogether eliminated. Consequently, the novel features of the present invention provide a tongue cleaner for not only cleansing the tongue and palate, but also creating a pleasant oral sensation that encourages the user to initiate and maintain a regular regime of lingual hygiene.

None of the above inventions and patents, taken either singly or in combination, is seen to describe the instant invention as claimed.

SUMMARY OF THE INVENTION

The present invention is a tongue cleaning device that provides the user (either for personal use or use by the oral hygienist) a device that is safe, comfortable to use, and sanitary. Along with important qualities of sanitation, the present invention is pleasant to use. A plurality of broadened cleaning ribs and an overall flattened configuration reduce, if not altogether eliminate the gag reflex when the present invention is drawn across the surface of the tongue. Importantly, the unique configuration of the present invention maximizes the physical comfort and pleasure the user will experience when cleansing the tongue. Users will, therefore, be inclined to take up a regular regime of improved oral hygiene.

A tongue cleaning device according to the present invention comprises a cleaning head that is integral with an elongate handle. Preferably the handle has a first portion which is disposed for gripping by a user and a second portion integral with the first portion and connected to the cleaning head. The first portion is inclined with respect to the second portion by an angle of inclination within the range of 135° and 165°, and more preferably about approximately 150°. The cleaning head is relatively flat and broad, having a plurality of cleaning ribs depending from a lower surface thereof. Each rib has a cleaning surface distal from the lower surface of the cleaning head. According to one embodiment, the cleaning surface comprises a pair of conterminous converging faces that meet and integrally connect along an apex that extends the length of each rib. The sharpness of the apex is determined by the angle of convergence between the converging faces, and preferably the angle of convergence is nonacute (greater than or equal to 90°). According to a second embodiment, the cleaning surface on each of the ribs is arched.

The entire tongue cleaning device is formed of a polymeric material that may be sterilized (i.e. by chemical treatment, ultraviolet irradiation, or high temperature and pressure autoclave). A preferred polymeric material for forming the tongue cleaning device is a food grade plastic that can withstand the high temperatures inherent during autoclave sterilization.

Accordingly, it is a principal object of the invention to provide a tongue cleaner that effectively removes from the surface of the tongue malodorous residues and unhealthy films.

It is another object of the invention to provide a tongue cleaner that is easy and pleasant to use, which moreover, encourages a regular regime of complete oral hygiene.

It is a further object of the invention to provide a device that is made from a polymeric material that is of a food grade quality and that can be sterilized.

Still another object of the invention is to provide a tongue cleaner having a cleaning head with a plurality of cleaning ribs that provide uniform pressure across the surface of the tongue during cleaning.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
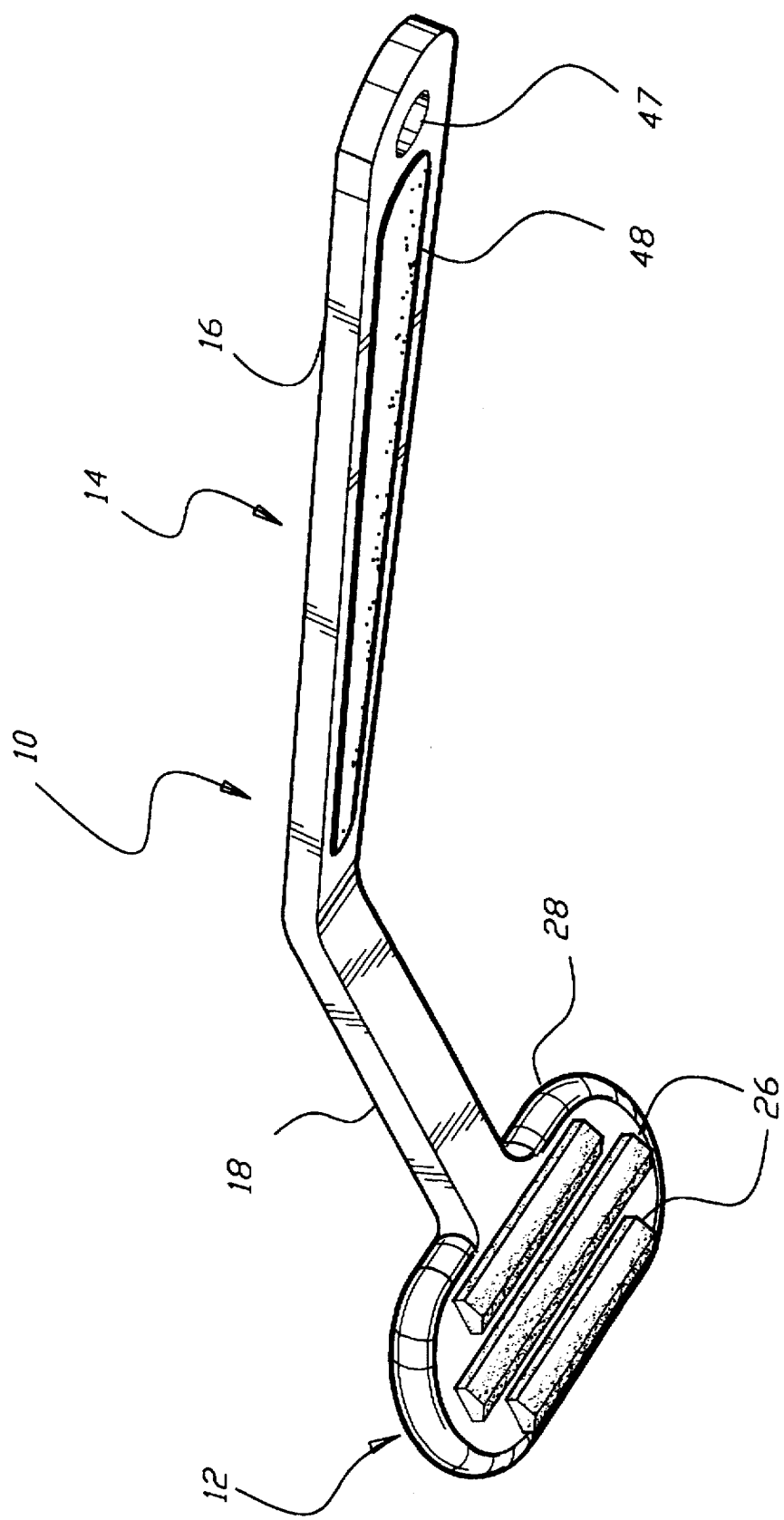
FIG. 1 is a perspective view of the tongue cleaning device.

Referring to the figures by numerals of reference, and first to FIGS. 1–3, 10 denotes generally a tongue cleaning device according to the present invention. The tongue cleaning device generally comprises a cleaning head 12 that is integral with an elongate handle 14. Preferably the entire tongue cleaning device 10 is formed of a polymeric material that may be sterilized (i.e. by chemical treatment, ultraviolet irradiation, or high temperature and pressure autoclave). A preferred polymeric material for forming the tongue cleaning device 10 is a food grade plastic, which is either molded or extruded to form the device. It should be apparent from the description below, however, that other polymeric materials may also be used to form the tongue cleaning device of the present invention.

The handle 14 may be linear, however, to facilitate ease of use for the tongue cleaning device it is preferable for the handle to be bent. Thus, the handle 14 has a first portion 16 which is disposed for gripping by a user of the device and a second portion 18 integral with the first portion and connected to the cleaning head 12. The first portion is inclined with respect to the second portion by an angle of inclination α (shown in FIG. 3), which preferably is within the range of 135° and 165°, and more preferably about approximately 150°. The angle of inclination is adapted specifically to permit the use of the present invention without hitting or abrading the rear portion of the soft palate, which may induce serious discomfort for the user.

Figure 2:
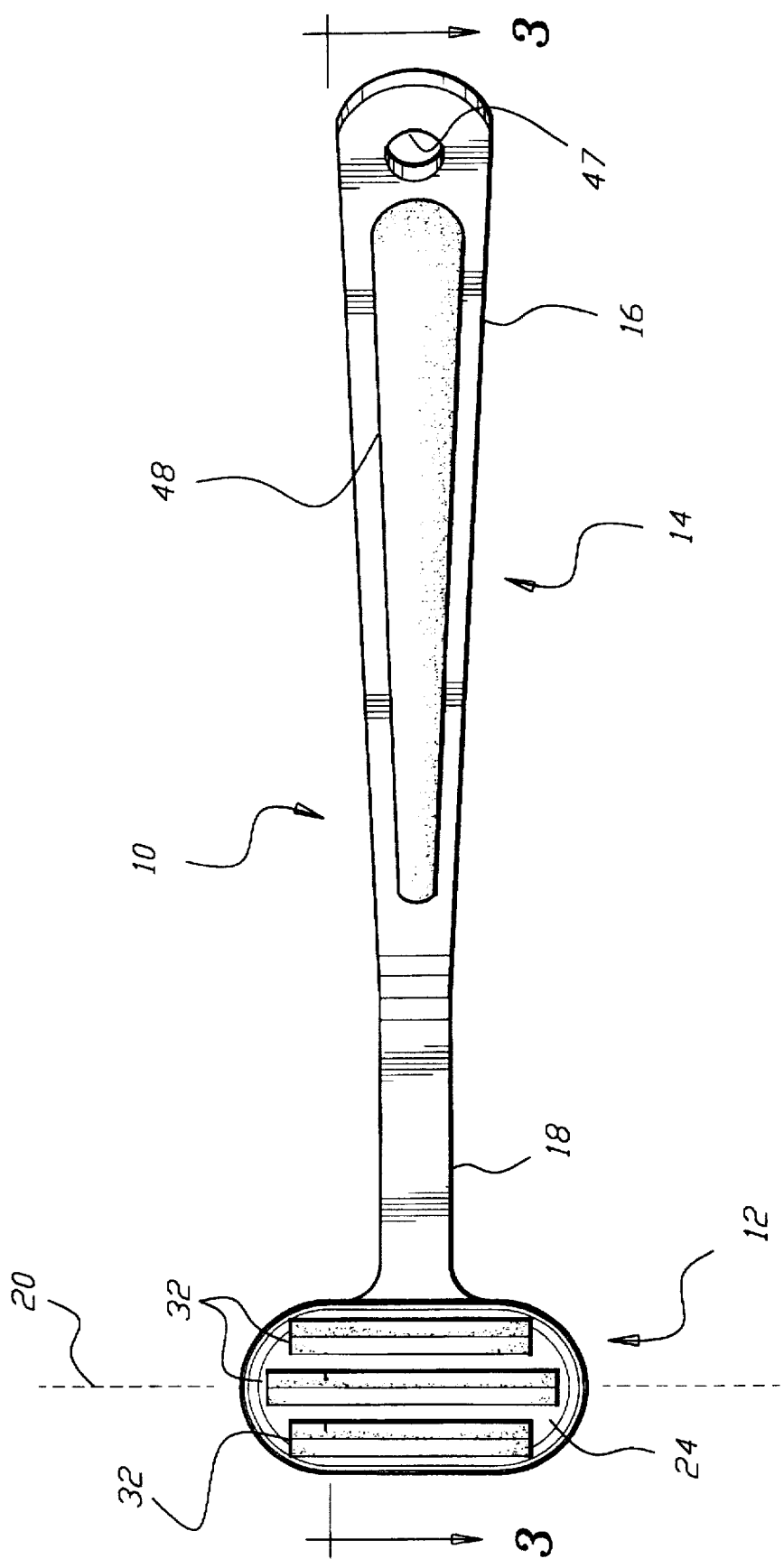
FIG. 2 is bottom view of the tongue cleaning device showing the cleaning ribs located on the lower surface of the cleaning head.
Figure 3:
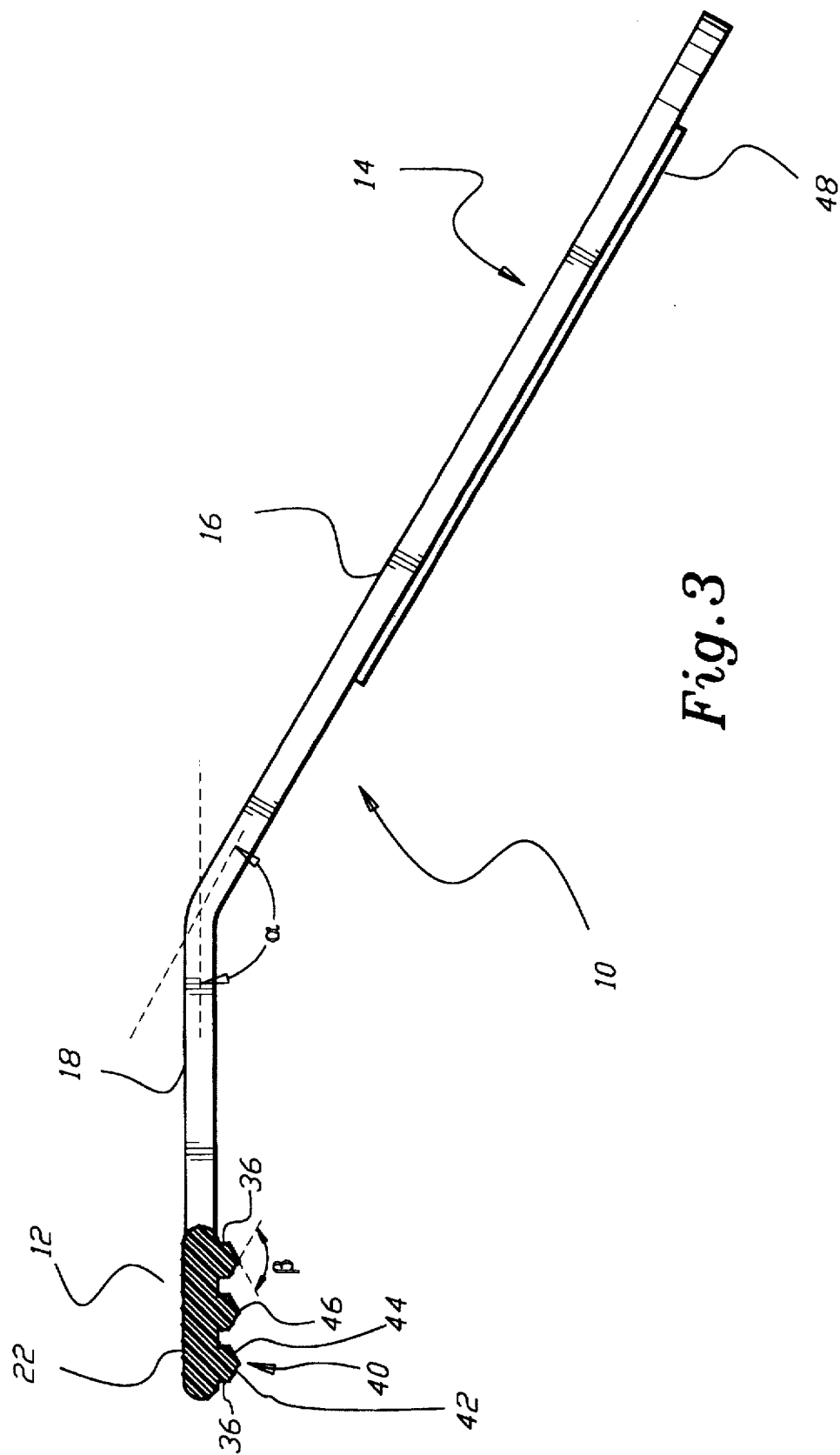
FIG. 3 is a partial cross sectional view of the tongue cleaner according to line 3—3 in FIG. 2 showing a cross section of the cleaning ridges and an elevational view of the handle which illustrates the angle of inclination between the first and second portions of the handle.

Referring specifically now to FIG. 2, the cleaning head 12 is shown with its longitudinal axis 20 oriented in a perpendicular relationship to the handle 14. The cleaning head is relatively flat and broad, having a flat upper surface 22 (shown in FIG. 3) and a lower surface 24, as well as a smooth, continuous rounded edge 28 about its perimeter. Depending from the lower surface 24 is a plurality of cleaning ribs 26 which are oriented in the direction of the longitudinal axis 20. As shown in the embodiment of FIGS. 1–3, three such ribs are present in parallel spaced relation on the lower surface of the cleaning head. Due to the shape of the cleaning head, the ribs 26 are not equal in length. Instead, the length of each rib differs from the adjacent rib, however, each rib extends the length of the cleaning head without interfering with the continuous rounded edge 28.

Each rib 26 has opposed ends 32 with opposed lateral surfaces 36 extending the length of each rib (between the opposed ends 32) integral with the lower surface. Projecting outwardly from between the opposed lateral surfaces 36 on each rib 26 is a cleaning surface 40 which is distal from the lower surface. The cleaning surface 40 on each rib 26 is identical for the three ribs shown on the embodiment of FIGS. 1–3. The preferred cleaning surface 40 comprises a pair of conterminous converging faces 42 and 44 that meet and connect along an apex 46 that extends the length of each rib. As shown in FIG. 3, the sharpness of the apex is determined by the relationship between the converging faces 42 and 44. More specifically, the sharpness of the apex is determined by the angle of convergence β of the converging faces 42 and 44. Preferably the angle of convergence is nonacute, or greater than or equal to 90°. An angle of convergence which is nonacute prevents the cleaning surface from irritating the tissues of the mouth or causing user discomfort when the tongue cleaning device is used.

In addition to the above features, the handle 14 of each tongue cleaning device is provided with an aperture 47 that passes through the first portion 16 of the handle. Aperture 47 allows for suspension storage of the tongue cleaning device 10 (i.e., on a hook or the like) when the device is not is use. The first portion also is provided with gripping means in the form of a rubberized laminae 48 adhesively secured to the first portion of the handle. The rubberized laminae 48 facilitates gripping of the handle during use of the tongue cleaning device 10.

Figure 4:
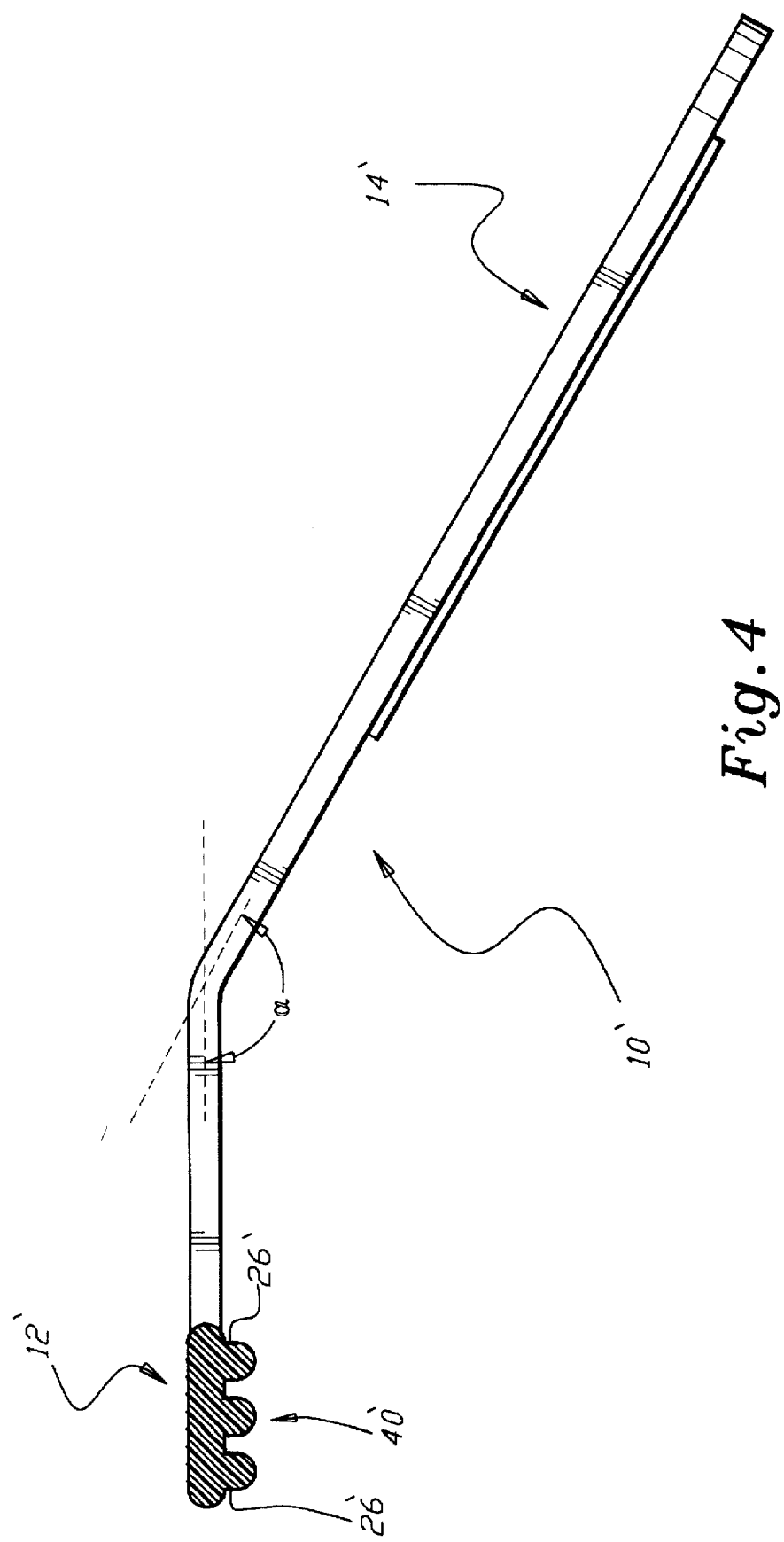
FIG. 4 is side elevational view of a second embodiment of the tongue cleaning device, with the cleaning head shown in cross section as in FIG. 3.

According to a second embodiment shown in FIG. 4, a different cleaning rib 26' is shown. Instead of having a pair of converging faces which form a distinct apex, the cleaning surface 40' is arched. The arched cleaning surface is sufficient to remove debris from the surface of the tongue, however, it is even less likely to cause irritation or other damage to tissues of the mouth.

In use, a user (either an individual or a trained professional) may grasp the tongue cleaning device 10 about the first portion 16 of the handle, and place the cleaning head 12 into the mouth with the cleaning surfaces 40, 40' of the ribs resting against the tongue. With the angled handle having an angle of inclination (between the first portion and second portion) of about approximately 150°, the cleaning head of the present invention may easily reach the back of the tongue. To clean the tongue, a user will move the device along the surface of the tongue with inward and outward movement to cause the cleaning surfaces of the ribs to remove debris and other deposits from the surface of the tongue.

Following use of the tongue cleaning device 10, a professional hygienist likely will desire to sterilize the device for later usage. The tongue cleaning device may be washed in a chemical detergent bath to remove any debris from the cleaning head, and then sterilized so that the device may be used again. Sterilization may occur by any process, such as chemical disinfection, ultraviolet irradiation, or high temperature sterilization by an autoclave or the like. The food grade plastics used to make the tongue cleaning device of the preferred embodiment is capable of withstanding the effects of high temperature sterilization in an autoclave.

Because the ribs do not have a sharp cleaning surface, there is little, if any, risk of causing irritation or other damage to the tissues of the mouth. Instead, the cleaning surfaces stimulate the tissue of the tongue to cause a pleasant oral sensation. In addition, because the cleaning head is substantially flat and relatively broad, it is difficult and unlikely that insertion of the device into the mouth will cause the cleaning head to strike the back of the throat. Thus, the likelihood of discomfort (i.e., gagging or retching) is substantially reduced. Furthermore, any contact that occurs between the rounded edge of the cleaning head and tissues of the mouth (i.e., cheeks or gums) is also unlikely to result in significant trauma to the tissue.

It is to be understood that the present invention is not limited to the sole embodiment described above, but encompasses any and all embodiments within the scope of the following claims.

I claim:

1. A tongue cleaning device, comprising:
   an elongate handle;
   a flat broad cleaning head integral with said handle, said cleaning head having rounded edges and a longitudinal axis oriented perpendicular to said handle, said cleaning head having a lower surface; and
   a plurality of cleaning ribs depending from said lower surface, each of said cleaning ribs being oriented in the direction of said longitudinal axis, and each of said cleaning ribs having a blunt cleaning surface distal from said lower surface.

2. The tongue cleaning device according to claim 1, wherein said handle has a first portion for gripping by a user and a second portion integral with said first portion which connects said handle to said cleaning head.

3. The tongue cleaning device according to claim 2, wherein said first portion is inclined with respect to said second portion by an angle of inclination.

4. The tongue cleaning device according to claim 3, wherein said angle of inclination is between 135° and 165°.

5. The tongue cleaning device according to claim 4, wherein said angle of inclination is around 150°.

6. The tongue cleaning device according to claim 2, further comprising gripping means secured to said first portion of said handle to assist a user in gripping said first portion of said handle.

7. The tongue cleaning device according to claim 6, wherein said gripping means comprises a rubberized laminae.

8. The tongue cleaning device according to claim 1, wherein said handle has an aperture therethrough for suspension storage of said tongue cleaner during periods of nonuse.

9. The tongue cleaning device according to claim 1, wherein said tongue cleaning device is formed of a polymeric material.

10. The tongue cleaning device according to claim 9, wherein said polymeric material is a food grade plastic.

11. The tongue cleaning device according to claim 1, wherein said cleaning ribs are substantially parallel to one another.

12. The tongue cleaning device according to claim 1, wherein said cleaning surface on each of said cleaning ribs is convex.

13. The tongue cleaning device according to claim 1, wherein said cleaning surface on each of said cleaning ribs is formed of a pair of outwardly projecting, conterminous, converging surfaces that connect along a linear apex, said converging surfaces having an angle of convergence which is nonacute.

* * * * *